US009700501B2

(12) United States Patent
Anzali et al.

(10) Patent No.: US 9,700,501 B2
(45) Date of Patent: Jul. 11, 2017

(54) USE OF INDOLE COMPOUNDS AS A COSMETIC

(71) Applicant: MERCK PATENT GESELLSCHAFT MIT BESCHRANKTER HAFTUNG, Darmstadt (DE)

(72) Inventors: Soheila Anzali, Gross-Zimmern (DE); Francis Contard, Lyons (FR); Jean Jacques Zeiller, Lyons (FR)

(73) Assignee: Merck Patent GmbH, Darmstadt (DE)

( * ) Notice: Subject to any disclaimer, the term of this patent is extended or adjusted under 35 U.S.C. 154(b) by 848 days.

(21) Appl. No.: 13/657,312

(22) Filed: Oct. 22, 2012

(65) Prior Publication Data
US 2013/0045174 A1    Feb. 21, 2013

Related U.S. Application Data

(62) Division of application No. 13/057,284, filed as application No. PCT/EP2009/005522 on Jul. 30, 2009, now abandoned.

(30) Foreign Application Priority Data

Aug. 9, 2008  (EP) ..................... 08014256

(51) Int. Cl.
| | |
|---|---|
| A61K 8/49 | (2006.01) |
| A61K 31/404 | (2006.01) |
| A61P 29/00 | (2006.01) |
| A61P 17/10 | (2006.01) |
| A61P 17/00 | (2006.01) |
| A61Q 17/04 | (2006.01) |
| A61Q 5/00 | (2006.01) |
| A61Q 19/08 | (2006.01) |
| A61Q 19/00 | (2006.01) |
| A61Q 19/02 | (2006.01) |

(52) U.S. Cl.
CPC .............. *A61K 8/492* (2013.01); *A61Q 17/04* (2013.01); *A61Q 19/007* (2013.01); *A61Q 19/02* (2013.01); *A61Q 19/08* (2013.01)

(58) Field of Classification Search
CPC ............................. C07D 209/42; A61K 31/14
USPC .......................................... 514/419; 424/601
See application file for complete search history.

(56) References Cited

U.S. PATENT DOCUMENTS

| | | |
|---|---|---|
| 4,069,338 A | 1/1978 | Schacht et al. |
| 2009/0110746 A1 | 4/2009 | Gainer et al. |
| 2009/0196893 A1 | 8/2009 | Tranchant et al. |

FOREIGN PATENT DOCUMENTS

| | | |
|---|---|---|
| WO | 2007132129 A2 | 11/2007 |

OTHER PUBLICATIONS

Langley et al., "Psoriasis: epidemiology, clinical features, and quality of life." Ann Rheum Dis 2005;64(Suppl II):ii18-ii23.*
International Search Report for PCT/EP2009/005522 mailed Dec. 8, 2009.
Wiechers et al., "A new mechanism of action for skin whitening agents: binding to the peroxisome proliferator-activated receptor," International Journal of Cosmetic Science, 2005, vol. 27, pp. 123-132.

* cited by examiner

*Primary Examiner* — Walter Webb
(74) *Attorney, Agent, or Firm* — Millen White Zelano and Branigan, PC; Csaba Henter; Anthony Zelano

(57) ABSTRACT

The invention relates to a compound of formula I

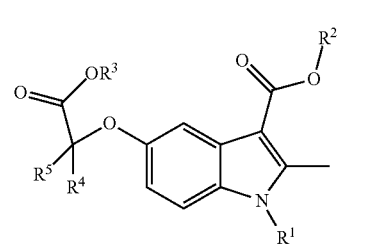

wherein $R^1$, $R^2$ and $R^3$ are identical or different and each is H or alkyl of 1-6 carbon atoms, $R^4$ is H or methyl, $R^5$ is phenyl or chlorophenyl, and/or physiologically acceptable salts thereof and its use in compositions, especially topical, cosmetic and/or personal care compositions, and compositions containing said compound.

16 Claims, 1 Drawing Sheet

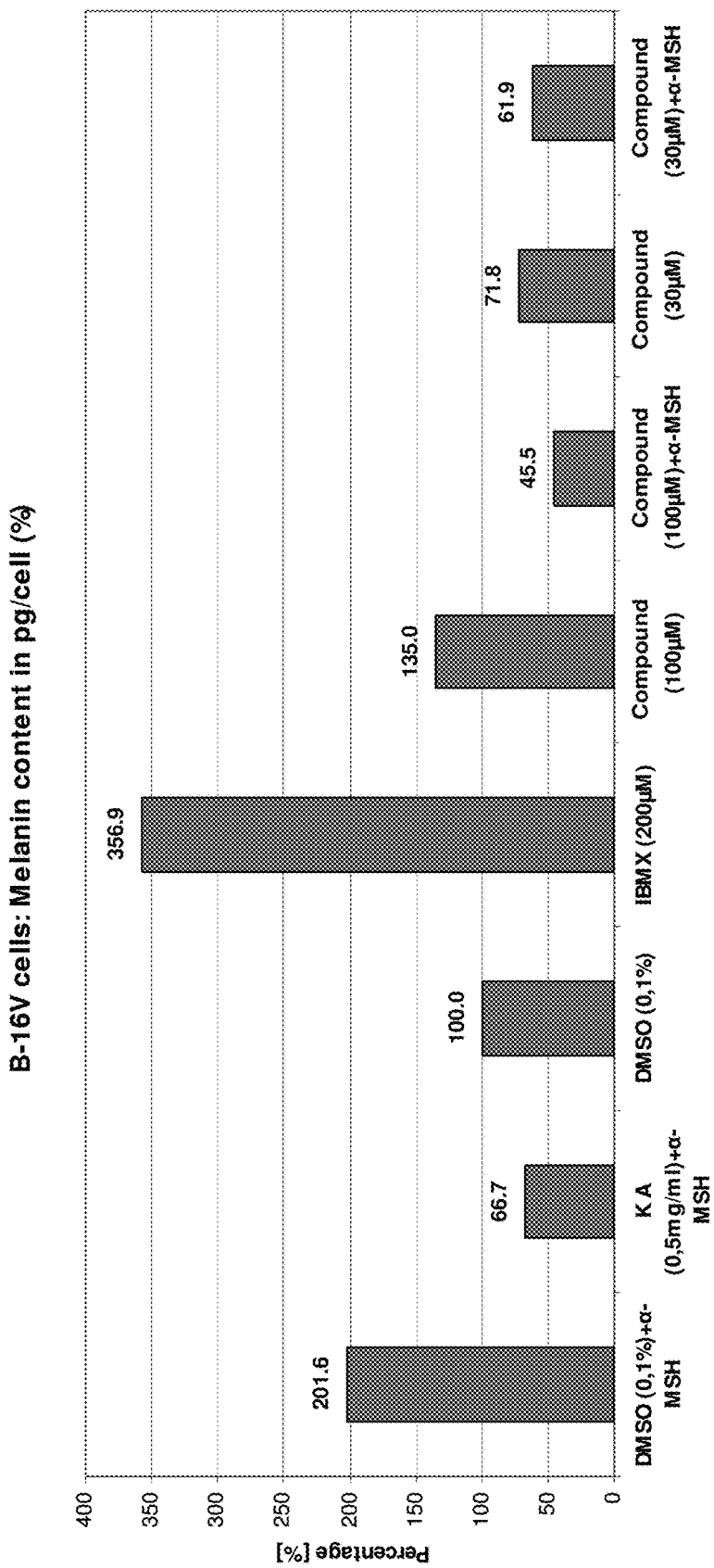
Fig. 1: B-16V cells: % of Melanin content in pg/cell. DMSO is the solvent and used as negative control. IBMX (3-Isobutyl-1-methylxantine) is the positive control. Kojic acid (KA) is the known reference ingredient for skin whitening.

USE OF INDOLE COMPOUNDS AS A COSMETIC

This application is a divisional application of U.S. Ser. No. 13/057,284 filed Feb. 3, 2011.

The present invention relates to a indole compound of formula I and its use in compositions, especially topical, cosmetic and/or personal care compositions, and compositions containing said compound.

The human skin is subject to certain ageing processes, some of which are attributable to intrinsic processes (chronoageing) and some of which are attributable to exogenous factors (environmental, for example photoageing). In addition, temporary or even lasting changes to the skin picture can occur, such as acne, greasy or dry skin, keratoses, rosaceae, light-sensitive, inflammatory, erythematous, allergic or autoimmune-reactive reactions, such as dermatosis and photormatosis.

The exogenous factors include, in particular, sunlight or artificial radiation sources having a comparable spectrum, and compounds which can be formed by the radiation, such as undefined reactive photoproducts, which may also be free-radical or ionic. These factors also include cigarette smoke and the reactive compounds present therein, such as ozone, free radicals, for example the hydroxyl free radical, singlet oxygen and other reactive oxygen or nitrogen compounds which interfere with the natural physiology or morphology of the skin.

The influence of these factors can result, inter alia, in direct damage to the DNA of the skin cells and to the collagen, elastin or glycosaminoglycan molecules of the extracellular matrix, which are responsible for the strength of skin. In addition, the signal transduction chains, which are terminated by the activation of matrix-degrading enzymes, may be affected. Important representatives of these enzymes are the matrix metalloproteinases (MMPs, for example collagenases, gelatinases and stromelysins), whose activity is additionallly regulated by TIMPs (tissue inhibitors of matrix metalloproteinases).

The consequences of the above-mentioned ageing processes are thinning of the skin, weaker interlacing of epidermis and dermis, and a reduction in the number of cells and the supplying blood vessels. These results in the formation of fine lines and wrinkles, the skin becomes leathery, and pigment defects can occur.

The same factors also act on hair, where damage can likewise occur. The hairs become brittle, less elastic and dull. The surface structure of the hairs is damaged.

Cosmetic or dermatological care products having properties which are claimed to counter the processes described or comparable processes or reduce or reverse the harmful consequences thereof are frequently distinguished by the following specific properties—free-radical-scavenging, antioxidative, inflammation-inhibiting or humectant. They prevent or reduce, inter alia, the activity of matrix-degrading enzymes or regulate the new synthesis of collagen, elastin or proteoglycans.

The above-mentioned ageing processes result in a thinning of the skin, the decrease of serration between epidermis and dermis, reduction of the cell number as well as the reduction of the supplying blood vessels. These processes are accompanied by the formation of lines and wrinkles, the skin becomes leather-like and/or shows pigmentary abnormalities.

Those factors also effect the status of the hair, resulting as well in a damage of the hair, especially damages in the surface of the hair that lead to brittleness and the loss of elasticity and gloss of the hair.

Care products and/or cosmetic products with properties that shall counteract against the described or similar processes and/or that shall reverse the damaging results often sure one or more of the following properties: free radical scavenging, anti-oxidative, anti-inflammatory and/or moisturising. Preferably, they block or reduce the activity of the matrix-disintegrating enzymes or control the denovo-synthesis of collagen, elastin and/or proteoglycans.

The use of antioxidants or free-radical scavengers in cosmetic compositions is adequately known per se. Thus, the use of the antioxidative vitamin E in sunscreen formulations is usual. Nevertheless, the effect achieved is even here well short of the hoped-for effect.

Vitamin A and vitamin-A derivatives, such as retinoic acid, retinol and retinol esters, act on the differentiation of epithelial cells and are therefore employed for the prophylaxis and treatment of numerous phenomena which impair the skin state, for example use against acne, psoriasis, senile keratosis, skin discoloration and wrinkles has been described (cf., for example, WO 93/19743 and WO 02/02074).

However, a skin-irritant effect of retinol and derivatives is also described in the literature (for example WO 94/07462). These side effects restrict the use of retinol to narrowly limited areas, it being necessary to avoid overdosing. There is therefore a demand for active ingredients which have a retinol-like spectrum of action, but do not have the side effects described or at least only do so in reduced form.

The compound for use according to the instant invention has the formula I

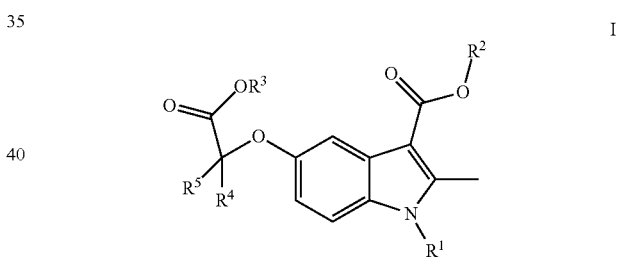

wherein
$R^1$, $R^2$ and $R^3$ are identical or different and each is H or alkyl of 1-6 carbon atoms,
$R^4$ is H or methyl,
$R^5$ is phenyl or chlorophenyl,
and physiologically acceptable salts thereof.

Alkyl is unbranched (linear) or branched, and has 1, 2, 3, 4, 5 or 6 C atoms. Preferably alkyl denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-tri-methylpropyl. Preferably alkyl denotes alkyl having 1, 2, 3 or 4 C atoms, especially methyl, ethyl, n-propyl, isopropyl, butyl, isobutyl, sec-butyl, tert-butyl, particularly preferred is methyl, ethyl, n-propyl and isopropyl.

The compound of formula I can be used as free acid but also as one of its salts with organic or inorganic bases, of the salts formed with metals and in particular alkali, alkaline earth and transition metals (such as sodium, potassium calcium, magnesium or aluminium) or with bases, such as ammonia or secondary or tertiary amines (such as diethylamine, triethylamine, piperidine, piperazine or morpholine), or with basic amino acids or with osamines (such as meglumine) or with aminoalcohols (such as 3-aminobutanol and 2-aminoethanol).

In a preferred embodiment of the invention the compound for use according to the instant invention is a compound of sub-formulae Ia to Ih, which conform to the formula I and in which the radicals not designated in greater detail have the meaning indicated for the formula I, but in which
in Ia $R^1$ is H or alkyl of 1-4 carbon atoms
in Ib $R^1$ is H, methyl, ethyl, n-propyl, isopropyl or isobutyl,
in Ic $R^2$ is H, methyl or ethyl,
in Id $R^2$ is H,
in Ie $R^2$ is methyl or ethyl,
in If $R^3$ is H, methyl or ethyl,
in Ig $R^3$ is H,
in Ih $R^3$ is methyl or ethyl.

Furthermore, particular preference is given to all physiologically compatible salts of the compounds which come under one or more of formulae I, Ia, Ib, Ic, Id, Ie, If, Ig and/or Ih.

In a specifically preferred embodiment of the invention the compound for use according to the instant invention is 2-Phenyl-2-(1-isobutyl-2-methyl-3-ethoxycarbonyl-5-indolyloxy)-propionic acid and/or a physiologically acceptable salts thereof.

The compound of formula I has been previously disclosed in U.S. Pat. No. 4,069,338, the whole disclosure of which is hereby incorporated to the present application by reference. According to U.S. Pat. No. 4,069,338 the compound of formula I is effective to lower the cholesterol level in the product of mammals.

Suprisingly, it has been found by the present invention that the compound of formula I is a peroxisome proliferator-activated receptors (PPAR) ligand, in particular PPAR-alpha and -gamma activator.

For compounds acting via "PPAR activation" it has been described that they may be usable as anti-ageing agents.

It has been shown that PPAR-alpha activator are responsible for epidermal differentiation (increased levels of filaggrin and involucrin). PPAR ligands like Oleic acid, linoleic acid and clofibrate accelerated the development of the stratum corneum and epidermal barrier in fetal skin explants derived from rats [Günther Weindl et al., Drugs 2005, 65 (14), 1919-1934].

PPAR-alpha agonists causes reduced inflammation via the reduction of interleukin-1alpha (IL-1a), also PPAR-alpha-induced reduction of IL-1alpha could result in less melanin being produced and thus incorporated per cell [J. W. Wiechers et al., International Journal of Cosmetic Science, 2005, 27, 123-132].

PPAR activators like Clofibrate increases the expression of profilaggrin, a major constituent of keratohyalin granules, increases the processing of profilaggrin to filaggrin, and increases the expression of loricrin, a key strructural protein of the cornified envelope. Furthermore they induced differentiation in human keratinocyte cultures, as indicated by increased protein and m-RNA levels of 2 differentiation-specific proteins: involucrin and transglutaminase. Similar to other inducers of differentiation, such as vitamin D derivates and retinoic clofibrate inhibits keratinocyte growth and proliferation in vitro and in vivo [Hanley K, et al., J Invest Dermatol 1998 April; 110 (4): 368-75 and Komuves L G, J Invest Dermatol 2000 September; 115 (3): 353-60]

PPAR-alpha might be important for the development of the epidermis during late embryogenesis, but dispensable for renewal of the epidermis in the adult animal [L. Michalik, W. Wahli, Biochimica et Biophysica Acta 1771 (2007) 991-998].

Interestingly, the PPAR-alpha agonist clofibrate, within a narrow range of concentrations, increases the survival of human hair follicles [L. Michalik, W. Wahli, Biochimica et Biophysica Acta 1771 (2007) 991-998].

More recently, PPAR activators (PPAR-alpha: clofibrate; PPAR-beta/delta; GW501516; PPAR-gamma: ciglitazone, troglitazone or G1262570) were reported to increase the expression of a key enzyme of keratinocyte differentiation and epidermal barrier maturation, namely, the cholesterol sulfotransferase type 2B1b[L. Michalik, W. Wahli, Biochimica et Biophysica Acta 1771 (2007) 991-998].

PPAR-alpha favours skin healing via modulation of the inflammatory phase, while PPAR-beta is an important player of keratinocyte survival and migration.

Consistently, transgenic mice overexpressing PPAR-alpha in the epidermis show reduced hyperplasia upon topical application of TPA, suggesting that PPAR-alpha prevents hyperproliferation of keratinocytes in adult mouse skin [Q. Yang et al, J. Invest. Dermatol. 126 (2006) 374-385.]

Reduced inflammation via the reduction of interleukin-1alpha (IL-a), therefore is skin tanning as a reaction to UV-induced irradiation. In the short term, upregulating the p38 pathway leads to increased tyrosinase production. In the long-term frame, inflammatory cytokines such as IL-alpha act in a communicative way on melanocytes that also increases tyrosinase levels. PPAR-alpha-induced reduction of IL-1 alpha could therefore result in less melanin being produced and thus incorporated per cell[J. W. Wiechers et al., International Journal of Cosmetic Science, 2005, 27, 123-132]

PPAR gamma activators inhibit melanoma proliferation in a dose-dependent manner (reduced tyrosinase production and/or a reduced tyrosinase half-life. PPAR-alpha and -gamma are upregulated in the interfollicular epidermis of mice during the wound healing or proliferation induced by topical application of 12-o-tetradecanoyl-phorbol-13-acetate (TPA)[Günther Weindl et al., Drugs 2005, 65 (14), 1919-1934,].

TNF-α released by injured epidermal keratinocytes activates stress-associated protein kinase (SAPK) and induces AP-1 binding to the PPARδ (PPAR-delta or PPAR-beta) promoter and transcription of PPARδ target genes. TNF-α also triggers production of endogenous PPARδ ligands, which activate PPARδ in keratinocytes and macrophages.

PPARδ activation helps maintain a sufficient number of keratinocytes for reepithelialization by improving apoptosis resistance through expression of integrin-linked kinase (ILK) and 3-phosphoinositide-dependent kinase (PDK), as well as via activation of the PKB/Akt-1 survival pathway. The initial inflammatory signals that stimulate PPARδ are countered by TGF-β1/Smad3-mediated suppression of PPARδ in the late re-epithelialization/remodeling stage. This suppression occurs via Smad3/4 complex-mediated abrogation of AP-1 activity. In addition, TGF-β1 released by dermal wound fibroblasts increases macrophage numbers and stimulates ECM production for wound remodelling [L. Michalik, W. Wahli, Biochimica et Biophysica Acta 1771 (2007) 991-998]

PPAR activators are the new mechanism of action for skin lightening and/or whitening. Activators of PPAR receptor are known as a skin whitening agent. Binding of activators to PPAR-gamma may reduced the melanogenesis. Binding to PPAR-gamma in turn results in less tyrosinase being formed. This in turn leads to reduced melanogenesis both in vitro and in vivo because the compound of formula I binds not only to PPAR-gamma but also to PPAR-alpha.

Binding of ligand to the nuclear receptor PPAR may lead to release of BCL-6, a transcriptional repressor of inflammation. This may result in decreased expression of inflammatory cytokine genes, reduced inflammation, and a decrease in atherosclerosis [L. Michalik, W. Wahli, Biochimica et Biophysica Acta 1771 (2007) 991-998].

Cosmetic peroxisome proliferator-activated receptor (PPAR) lipids have been shown to significantly improve the photoaged appearance of skin, versus a vehicle effect, and, in combination with glycolic acid, versus glycolic acid alone [J. W. Wiechers et al., International Journal of Cosmetic Science, 2005, 27, 123-132].

Owing to the constantly increasing demand for active ingredients for the preventative treatment of human skin and human hair against ageing processes and harmful environmental influences, the object of the present invention was to provide novel active ingredients which exhibit the effects already mentioned at the outset, are sufficiently oxidation- and photostable and can readily be formulated. The compositions prepared therewith should furthermore have as far as possible a low irritation potential for the skin, as far as possible have a positive influence on water binding in the skin, retain or increase skin elasticity and thus promote smoothing of the skin. In addition, they should preferably create a pleasant skin feeling on application to the skin. Preferably, a new active ingredient preferably shows one or more properties, selected from the group consisting of anti-ageing, anti-inflammatory, wrinkle preventing and wound healing properties. Preferably, it can be employed in products for capillary fragility treatment and/or prophylaxis, products for the treatment and/or prophylaxis of can, products for the treatment and/or prophylaxis of psoriasis, products for the treatment and/or prophylaxis of cellulite and/or Products for treatment and/or prophylaxis of grey hair.

It is known that PPAR-gamma agonists are involved in adipogenesis [Am J Physiol Endocrinol Metab 293:E1159-E1168, 2007]. It is also known that the development of adipocytes located around hair follicles in the fetal pig. The relationship between hair follicle development and adipocyte formation in the pig hypodermis was studied by Hausman G J et al [J. Animal Sci. 1982. 54:1286-1296]. They show that the development of hair follicle adipose lobules in the pig is associated temporally and spatially with hair follicle and sweat gland growth and development [J. Animal Sci. 1982. 54:1286-1296]. Accordingly the compound of formula I supposed to be involved in fat cells modulation and so, in hair follicle development.

The compound of formula I for use according to the instant invention is a novel active ingredient for the above discussed uses. Preferably, the compound of formula I for use according to the invention has advantageous properties, such as improved handling properties, improved stability properties and/or an advantageous profile of activation of PPAR-alpha and -gamma receptors.

The compound of formula I is in particular useful as anti-ageing, anti-inflammatory, acne and skin-whitening active and hair growth regulator ingredient, more particular as growth promoting agent, in dermatological and cosmetic compositions (alone or in combination with other actives). Therefore, the invention relates to the use of the compound of formula I for such purposes. Especially preferred is the use of the compound of formula I as skin lightening and/or skin whitening agent.

The invention also relates to the use of the compound of formula I in the preparation of cosmetic ingredients for the use as anti-geing, anti-inflammatory and for the treatment of acne, inducing or stimulating of hair growth and retarding hair loss and treatment of hyperpigmentation or for regulation of pigmentation (depigmentation).

The compound of formula I has been tested in vitro and shown increased expression of epidermal differentiation proteins, which also are known in the literature as indicators of improvement in skin condition and overall skin health [own unpublished results]

The term "dermatologically acceptable", as used herein, preferably means that the composition or components described suitable for use in contact with human skin without risk of toxicity, incompatibility instability, allergic response, and the like.

All terms such as "skin ageing", "signs of skin ageing", "topical application", and the like are preferably used in the sense in which they are generally and widely used in the art of developing, testing and marketing cosmetic and personal care products.

The term "cosmetic composition" or preferably more briefly just "composition" in accordance with the present invention preferably relates to a formulation that can be used for cosmetic purposes, purposes of hygiene and/or as a basis for delivery of one or more pharmaceutical ingredients. It is also possible that these formulations are used for two or more of these purposes at one time. Thus, the terms "cosmetics," "cosmetic composition" and/or "composition" as used herein, preferably include without limitation, lipstick, mascara, rouge, foundation, blush, eyeliner, lipliner, lip gloss, facial or body powder, sunscreens and blocks, nail polish, mousse, sprays, styling gels, nail conditioner, whether in the form of creams, lotions, gels, ointments, emulsions, colloids, solutions, suspensions, compacts, solids, pencils, spray-on formulations, brush-on formulations and the like. "Personal care products" preferably include, without limitation, bath and shower gels, shampoos, conditioners, cream rinses, hair dyes and coloring products, leave-on conditioners, sunscreens and sunblocks, lip balms, skin conditioners, cold creams, moisturizers, hair sprays, soaps, body scrubs, exfoliants, astringents, depilatories and permanent waving solutions, antidandruff formulations, antisweat and antiperspirant compositions, shaving, pre-shaving and after shaving products, moisturizers, deodorants, cold creams, cleansers, skin gels, rinses, whether in solid, powder, liquid, cream, gel, ointment, lotion, emulsions, colloids, solutions, suspensions, or other form. "Pharmaceutical preparations" in accordance with the present invention preferably include, without limitation, carriers for dermatological purposes, including topical and transdermal application of pharmaceutically active ingredients. These can be in the form of gels, patches, creams, nose sprays, ointments, lotions, emulsions, colloids, solutions, suspensions, powders and the like. Compositions in accordance with the invention preferably include cosmetics, personal care products and pharmaceutical preparations.

The terms "skin ageing" or "signs of skin ageing" preferably include, but are not limited to, all outward visibly and tactilely perceptible manifestations as well as any other macro or micro effects due to skin ageing. Such signs may be induced or caused by intrinsic factors or extrinsic factors, e.g. chronological ageing and/or environmental damage. The signs may result from processes which preferably include, but are not limited to, the development of textural discontinuities, such as wrinkles and coarse deep wrinkles, skin lines, crevices, bumps, large pores (e.g. associated with adnexal structures such as sweat gland ducts, sebaceous glands, or hair follicles), or unevenness or roughness of the skin, loss of skin elasticity (loss and/or in activation of functional skin elastin), sagging (including puffiness in the eye area and jowls), loss of skin firmness, loss of skin tightness, loss of skin recoil from deformation, discoloration (including (black) under eye circles), blotching, sallowness, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin. Particularly preferred in accordance with the present invention, the signs of skin aging are wrinkles and the compositions of the present invention are, in certain preferred embodiments, useful in fighting, treating or preventing wrinkles.

As used herein, prophylactically regulating a skin condition preferably includes delaying, minimizing and/or preventing visible and/or tactile discontinuities in skin (e.g., texture irregularities in the skin which may be detected visually or by feel), including signs of skin aging.

As used herein, therapeutically regulating skin condition preferably includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition.

Some of the products and compositions of the present invention are useful for improving skin appearance and/or feel of skin exhibiting signs of skin aging. For example, preferred compositions of the present invention are useful for regulating the appearance of skin conditions by providing an immediate visual improvement in skin appearance following application of the composition to the skin. Generally speaking, compositions of the present invention which further contain particulate materials will be most useful for providing the immediate visual improvement.

Some of the compositions of the present invention may also provide additional benefits, including stability, absence of significant (consumer-unacceptable) skin irritation, anti-inflammatory activity and good aesthetics.

In certain preferred aspects, the present invention is useful for improving the physiological state and/or the physical appearance of human skin, in particular to reduce the signs of skin aging that are generated by sun exposure, physical and hormonal stress, abrasion, nutritional effects and other similar causes. The compositions may often be used to prevent the signs of aging and/or to treat them in order to afford the consumer who uses them, a more youthful appearance.

Accordingly, the instant invention more preferably relates to:

A composition, preferably a non-therapeutic composition comprising the compound of formula I and/or a salt thereof.

A composition for topical use comprising
i) the compound of formula I and/or a salt thereof,
ii) one or more skin-tolerated vehicles, and optionally
iii) one or more further active compounds having a skin-care and/or inflammation-inhibiting action.

A composition for topical use comprising
i) the compound of formula I and/or a salt thereof,
ii) one or more skin-tolerated vehicles, and optionally
iii) one or more further active compounds having a skin-care and/or inflammation-inhibiting action.

A composition as described above/below, wherein the compound of formula I is contained in said composition in an amount of 0.00001 percent by weight to 10 percent by weight, preferably in an amount of 0.001 percent by weight to 10 percent by weight, more preferably in an amount of 0.1 percent by weight to 10 percent by weight, even more preferably 0.001 percent by weight to 5 percent per weight and especially 0.1 percent by weight to 5 percent by weight.

A composition comprising the compound of formula I and at least one further skin-care ingredient and at least one carrier which is suitable for topical applications.

Use of the compound of formula I for the manufacture of a composition, preferably a non-therapeutic composition and especially preferably a cosmetic composition or topical composition.

Use of the compound of formula I for the preparation of a composition which is suitable for the prophylaxis and/or treatment of skin diseases which are associated with defective keratinisation relating to differentiation and cell proliferation, in particular for the treatment of acne vulgaris, acne comedonica, polymorphic acne, acne rosaceae, nodular acne, acne conglobata, age-related acne, acne occurring as a side effect, such as acne solaris, medicament-related acne or acne professionalis, for the treatment of other defects of keratinisation, in particular ichthyosis, ichthyosiform states, Darier's disease, keratosis palmoplantaris, leukoplakia, leukoplakiform states, skin and mucosal (buccal) eczema (lichen), for the treatment of other skin diseases which are associated with defective keratinisation and have an inflammatory and/or immunoallergic component, and in particular all forms of psoriasis relating to the skin, mucous membranes and finger- and toenails, and psoriatic rheumatism and skin atopy, such as eczema, or respiratory atopy, or also hypertrophy of the gums.

Use of the compound of formula I for the care, preservation or improvement of the general state of the skin or hair.

Use of the Compound for hair care and/or hair follicle development.

Use of the compound of formula I for the prophylaxis against or reduction of skin unevenness, such as wrinkles, fine lines, rough skin or large-pored skin.

Use of the compound of formula I for the prophylaxis against time- and/or light-induced ageing processes of the human skin or human hair, in particular for prophylaxis against dry skin, wrinkle formation and/or pigment defects, and/or for the reduction or prevention of the harmful effects of UV rays on the skin.

Preferably, the compound of formula I and the compositions containing it preferably appear to have a benefit in tissue regeneration. This is believed to be due to their ability to modulate and preferably stimulate the production of certain advantageous biomolecules, including, but not limited to, collagen I, fibronectin, collagen IV and/or hyaluronic acid, in skin cells.

Thus, the compound of formula I and the compositions containing it can preferably be used to improve the visible signs of ageing in human skin, including fine lines, wrinkles, enlarged pores, roughness, dryness, and other skin texture defects such as the stretchmarks (as caused by pregnancy, trauma or other influences) bags under the eyes, also called "puffy eyes" and dark (under eye) circles, both preferably caused by thinning of the skin, insufficient blood circulation and/or slack tissue, especially on repeated topical application.

Thus, further subjects of the instant invention preferably comprise:

A method and/or a composition for reducing the visible signs of ageing, preferably for reducing the visible signs of ageing of the skin and/or hair, in an animal, preferably the human animal comprising:
applying to the animal showing signs of ageing, preferably to the portion of the skin and/or hair showing signs of ageing, a composition comprising the compound of formula I at least once a day for a period of time at least sufficient to provide a reduction of the visible signs of ageing, preferably the visible signs of ageing of the skin and/or hair. The period of time at least sufficient to provide the reduction of the visible signs of ageing generally is between one day and 12 months, preferably three days and six months, more preferably between two weeks and two months.

A method and/or a composition for reducing stretch marks of the skin, comprising:
applying to the skin, preferably at least to the portion of the skin showing stretchmarks, a composition comprising the compound of formula I at least once a day for a period of time at least sufficient to provide a reduction of the visible signs of stretch marks. The period of time at least sufficient to provide the reduction of the visible signs of stretch marks generally is between one day and 12 months, preferably three days and six months, more preferably between two weeks and two months.

A method and/or a composition for reducing stretch marks of the skin, comprising:
applying to the skin, preferably at least to the portion of the skin showing stretch marks, a composition comprising the compound of formula I at least once a day for a period of time at least sufficient to provide a reduction of the visible signs of stretch marks. The period of time at least sufficient to provide the reduction of the visible signs of stretch marks generally is between one day and 12 months, preferably three days and six months, more preferably between two weeks and two months.

A method and/or a composition for reducing dark circles under the eyes, comprising:
applying to the skin, preferably at least to the portion of the skin showing the dark circles, a composition comprising the compound of formula I at least once a day for a period of time at least sufficient to provide a reduction of the dark circles of the portion of human skin. The period of time at least sufficient to provide the reduction of the dark circles generally is between one day and 12 months, preferably three days and six months, more preferably between two weeks and two months.

One aspect of the present invention relates to the use of the compound of formula I for the protection of the skin against hair treatment agents, especially for the protection of the skin of the head against pigments, dyestuffs, dyes and/or colouring agents which are commonly used for colouring of the hair. During the treatment of the hair with cosmetic compositions the contact of the head treatment composition with the underlying skin is normally not completely avoidable. The contact of the head treatment composition with the underlying skin is especially disadvantageous in the case of hair colouring compositions, since the resulting colouration of the parts of the skin around the hair line and/or the roots of the hair is generally regarded as unesthetic and thus undesirous.

Thus, it is desirous to protect the skin from the negative effects of the hair treatment compositions. It is known in the art to use a variety compositions, such as emulsions, or other agents, such as vaseline, to achieve such a protection of the skin. However, the compositions and agents of prior art show only limited efficacy and/or have two be removed after the application of the head treatment composition. For example, vaseline is hard to remove from the skin and/or a hair due to its unsolubility in water. For a sufficient removal thereof, the use of strong detergents and/or organic solvents can become necessary, thereby affecting the intended result of the application of the hair treatment composition and/or having negative effect on the condition of the skin and/or hair.

According to the instant invention, the compound of formula I can be advantageously applied to protect the skin against hair treatment agents and especially to protect the skin of the head against adverse effects of pigments, dyestuffs, dyes and/or colouring agents, or hair colouring compositions in general.

Thus, a further subject of the instant invention is:

The use of the compound of formula I as described above/below for the protection of the skin against hair treatment agents, especially for the protection of the skin of the head against pigments, dyestuffs, dyes and/or colouring agents, or hair colouring compositions in general.

The use of the compound of formula I in a composition for the protection of the skin against hair treatment agents, especially for the protection of the skin of the head against pigments, dyestuffs, dyes and/or colouring agents, or hair colouring compositions in general.

The use of the compound of formula I for producing a preparation to protect the skin against hair-treatment compositions, preferably compositions which can dye, tint, shape, harden, condition, soften, repair or style hair, and especially compositions which can colour or tint the hair.

The use of the compound of formula I for the simultaneous protection of the skin against hair-treatment compositions and additionally for the care of the skin.

The compositions of the invention generally comprise the compound of formula I and one or more vehicle or carrier, preferably one or more cosmetically acceptable vehicle or carrier. The one or more vehicles or carriers may be independently selected from the group of hydrophobic and hydrophilic vehicles or carriers. Suitable, hydrophobic vehicles or carriers include, for example, waxy non-ionic substances, preferably waxy non-ionic substances commonly used in cosmetics, including, but not limited to esters and ethers of fatty alcohols and of fatty acids, with carbon chain length from $C_4$ to $O_{22}$, preferably from $C_8$ to $C_{18}$, and most preferably from $C_{12}$ to $C_{18}$. Examples of a fatty hydrophobic carriers or vehicles are preferably selected from the group consisting of isopropyl myristate, isopropyl palmitate, octyl palmitate, isopropyl lanolate, acetylated lanolin alcohol, the benzoate of $C_{12}$ to $C_{15}$ alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate, and isopropyl isostearate, and the like. Examples of hydrophilic carrier or vehicles, especially for solutions, are preferably selected from the group consisting of glycols and alkoxylated glycols, preferably glycols and alkoxylated glycols commonly used in cosmetics, including, but not limited to, ethylene glycol, diethylene glycol, triethylene glycol, propylene glycol, dipropylene glycol, and the like.

The compositions according to the invention, especially the cosmetic compositions according to the invention may be formulated as creams, lotions, serums, sprays, sticks and other forms known to those skilled in the art. Creams and lotions are the currently preferred product forms.

Preferably, the concentration of the compound of formula I in the cosmetically acceptable vehicle may range from 1 ppb to 10,000 ppm, preferably from 10 ppb to 1,000 ppm, more preferably from 100 ppb to 100 ppm, and most preferably from 1 ppm to 100 ppm.

Preferably, cosmetic compositions can typically comprise the carrier solution described above at levels between about 0.01% and about 90% by weight, preferably between about 0.1% and about 50%, more preferably between about 0.1% and about 20%, and more preferred still between about 1% and about 10% by weight.

Preferably, the concentration of the compound of formula I in the composition for application, preferably application to the skin and/or hair, may range from 1 ppb to 10,000 ppm, preferably from 10 ppb to 1,000 ppm, more preferably from 100 ppb to 100 ppm, even more preferably from 0.5 ppm to 150 ppm and most preferably 1 ppm to 100 ppm, for example about 0.5 ppm, about 1 ppm, about 1.5 ppm, about 5 ppm, about 10 ppm, about 25 ppm, about 50 ppm, about 75 ppm, about 100 ppm or about 125 ppm.

If applicable, ppb and ppm preferably are to be regarded to be based on the respective weights, such as of the weight of the respective components (e.g. compound of formula I, vehicle) and/or the weight of the respective component and the total weight of the composition. Accordingly, 1 ppm is preferably regarded as 1 mg/kg or $10^{-4}$% by weight.

Optionally, the compositions according to the invention may optionally comprise additional active and inactive ingredients other than the compound of formula I, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 and/or or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. In addition to the foregoing, the personal care products of the invention may contain any other compound for the treatment of skin disorders.

The invention also provides a method for ameliorating and/or preventing signs of human skin photo- and intrinsic aging comprising topically applying the cosmetic compositions of the invention. The cosmetic compositions of the invention are preferably applied to affected skin areas once or twice daily for as long as is necessary to achieve desired anti-aging results.

The present invention furthermore relates to compositions, preferably non-therapeutic compositions, comprising the compound of formula I and at least one further skin-care ingredient and at least one carrier which is suitable for topical applications, and to the use of the above-mentioned compounds for the care, preservation or improvement of the general state of the skin or hair.

Uses which are preferred in accordance with the invention are, in particular, the use for prophylaxis against time- and/or light-induced ageing processes of the human skin or human hair, in particular for prophylaxis against dry skin, wrinkle formation and/or pigment defects, and/or for the reduction or prevention of the harmful effects of UV rays on the skin, and for prophylaxis against or reduction of skin unevenness, such as wrinkles, fine lines, rough skin or large-pored skin.

Uses which are preferred in accordance with the invention are furthermore the use for the prophylaxis and/or prevention of premature skin ageing, in particular for the prophylaxis and/or prevention of light- or ageing-induced wrinkling of the skin, for the reduction of pigmentation and keratosis actinica, and for the prophylaxis and/or treatment of all diseases which are associated with normal skin ageing or light-induced ageing of the skin, and for the prophylaxis and/or treatment of skin diseases which are associated with defective keratinisation relating to differentiation and cell proliferation, in particular for the treatment of acne vulgaris, acne comedonica, polymorphic acne, acne rosaceae, nodular acne, acne conglobata, age-related acne, acne occurring as a side effect, such as acne solaris, medicament-related acne or acne professionalis, for the treatment of other defects of keratinisation, in particular ichthyosis, ichthyosiform states, Darier's disease, keratosis palmoplantaris, leukoplakia, leukoplakiform states, skin and mucosal (buccal) eczema (lichen), for the treatment of other skin diseases which are associated with defective keratinisation and have an inflammatory and/or immunoallergic component, and in particular all forms of psoriasis relating to the skin, mucous membranes and finger- and toenails, and psoriatic rheumatism and skin atopy, such as eczema, or respiratory atopy, or also hypertrophy of the gums, and for the prophylaxis and/or treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare.

The present invention also relates to the use of the compound of formula I for the preparation of compositions which are suitable for the above-mentioned uses.

The compositions here are preferably non-therapeutical, more preferably either compositions which can be used topically, for example cosmetic or dermatological formulations, or foods or food supplements. In this case, the compositions comprise a cosmetically or dermatologically or food-suitable carrier and, depending on the desired property profile, optionally further suitable ingredients.

The use according to the invention of the compound of formula I in compositions offers, inter alia, protection against damage caused directly or indirectly by UV radiation or by processes caused by reactive compounds, such as, for example, skin ageing, loss of skin moisture, loss of skin elasticity, formation of wrinkles or lines or of pigment defects or age spots.

The present invention furthermore relates to the use of the above-mentioned compositions for the prevention of undesired changes in the skin picture, such as, for example, acne or greasy skin, keratoses, light-sensitive, inflammatory, erythematous, allergic or autoimmune-reactive reactions.

However, the compound of formula I and compositions according to the invention preferably also serve for calming sensitive and irritated skin, for the preventative regulation of collagen, hyaluronic acid and elastin synthesis, stimulation of DNA synthesis, in particular in the case of deficient or hypoactive skin states, regulation of the transcription and translation of matrix-degrading enzymes, in particular of MMPs, increasing cell regeneration and regeneration of the skin, increasing the skin's own protective and repair mechanisms for DNA, lipids and/or proteins.

The compound of formula I is typically employed in accordance with the invention in amounts of from 0.01 to 20% by weight, preferably in amounts of from 0.1% by weight to 10% by weight and particularly preferably in amounts of from 1 to 8% by weight. The person skilled in the art has absolutely no difficulties in selecting the amount correspondingly depending on the intended action of the composition.

The protective action against oxidative stress or against the effect of free radicals can thus be further improved if the compositions comprise one or more further antioxidants, where the person skilled in the art has absolutely no difficulties in selecting antioxidants having a suitably fast or time-delayed action.

In a preferred embodiment of the present invention, at least one further skin-care ingredient is one or more antioxidants and/or vitamins.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to umol/kg), furthermore (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are furthermore described in WO 2006/111233 and WO 2006/111234.

Suitable antioxidants are also compounds of the general formula A and/or B

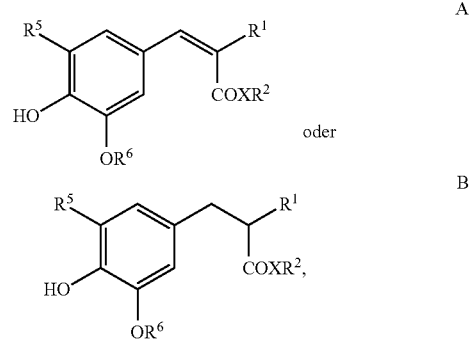

wherein
$R^1$ is selected from the group consisting of —C(O)CH$_3$, —CO$_2$R$^3$, —C(O)NH$_2$ and —C(O)N(R$^4$)$_2$,
X is O or NH,
$R^2$ is linear or branched Alkyl having 1 to 30 C-atoms,
$R^3$ is linear or branched Alkyl having 1 to 20 C-atoms,
$R^4$ is in each case independently selected from the group consisting of H and linear or branched Alkyl having 1 to 8 C-atoms,
$R^5$ is selected from the group consisting of linear or branched Alkyl having 1 to 8 C-atoms and linear or branched Alkoxy having 1 to 8 C-atoms and
$R^6$ is selected from the group consisting of linear or branched Alkyl mit 1 to 8 C-atoms bedeutet, preferably selected from derivatives of the 2-(4-Hydroxy-3,5-dimethoxybenzyliden)-malonic acid and/or 2-(4-Hydroxy-3,5-dimethoxybenzyl)-malonic acid, and especially preferably selected from 2-(4-Hydroxy-3,5-dimethoxybenzyliden)-malonic acid-bis-(2-ethylhexyl)ester (z.B. Oxynex® ST Liquid) and/or 2-(4-Hydroxy-3,5-dimethoxybenzyl)-malonic acid-bis-(2-ethylhexyl)ester (z.B. RonaCare® AP).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with the compound of formula I in compositions of this type in ratios in the range from 1000:1 to 1:1000, preferably in amounts of from 100:1 to 1:100.

The compositions according to the invention may comprise vitamins as further ingredients. The cosmetic compositions according to the invention preferably comprise vitamins and vitamin derivatives selected from vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin C and derivatives thereof, DL-α-tocopherol, tocopherol E acetate, nicotinic acid, pantothenic acid and biotin. Vitamins are usually employed here with the compound of formula I, in ratios in the range from 1000:1 to 1:1000, preferably in amounts of from 100:1 to 1:100.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxy-flavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N.J. Miller, G. Paganga, Trends in Plant Science 1997, 2(4), 152-159). K. Lemanska, H. Szymusiak, B. Tyrakowska, R. Zielinski, A. E. M. F. Soffers, I. M. C. M. Rietjens; Free Radical Biology&Medicine 2001, 31(7), 869-881, have investigated the pH dependence of the antioxidant action of hydroxyflavones. Quercetin exhibits the greatest activity amongst the structures investigated over the entire pH range.

Suitable antioxidants are furthermore compounds of the formula II

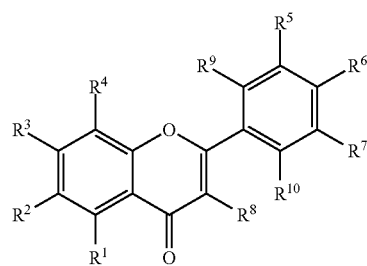

II where $R^1$ to $R^{10}$ may be identical or different and are selected from

H $OR^{11}$ straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3, where all $OR^{11}$ are, independently of one another,

OH straight-chain or branched $C_1$- to $C_{20}$-alkoxy groups, straight-chain or branched $C_3$- to $C_{20}$-alkenyloxy groups, straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, and/or $C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or mono- and/or oligoglycosyl radicals, with the proviso that at least 4 radicals from $R^1$ to $R^7$ are OH and that the molecule contains at least two pairs of adjacent —OH groups, or $R^2$, $R^5$ and $R^6$ are OH and the radicals $R^1$, $R^3$, $R^4$ and $R^{7-10}$ are H, as described in the earlier German patent application DE 10244282.7.

Besides the advantages mentioned above, the advantages of the compositions according to the invention comprising at least one antioxidant here are, in particular, the antioxidant action and the good skin tolerability. In addition, the compounds described here are preferably colourless or have only a weak colour and thus only result in slight discoloration of the compositions, or none at all.

Of particular advantage are compositions, preferably non-therapeutic compositions, comprising at least one compound of the formula II which is characterised in that at least two adjacent radicals of the radicals $R^1$ to $R^4$ are OH and at least two adjacent radicals of the radicals $R^5$ to $R^7$ are OH. Particularly preferred compositions comprise at least one compound of the formula II which is characterised in that at least three adjacent radicals of the radicals $R^1$ to $R^4$ are OH, preferably with the radicals $R^1$ to $R^3$ being OH.

It is also advantageous to administer the compounds of the formula II in encapsulated form, for example as cellulose or chitin capsules, in gelatine or wax matrices or encapsulated with cyclodextrins.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leucoplasia, leucoplasiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammations which are not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in tallow production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, and for the treatment of skin problems caused by UV radiation.

Compositions which are particularly preferred in accordance with the invention also comprise UV filters besides the compound of formula I.

In principle, all UV filters are suitable for combination with the compound of formula I. Particular preference is given to UV filters whose physiological acceptability has already been demonstrated. Both for UVA and UVB filters, there are many proven substances which are known from the specialist literature, for example:

benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl] benzyl}acrylamide (for example Mexoryl® SW), N,N,N-trimethyl-4-(2-oxoborn-3-ylidene-methyl)anilinium methylsulfate (for example Mexoryl® SK) or (2-oxoborn-3-ylidene)toluene-4-sulfonic acid (for example Mexoryl® SL), benzoyl- or dibenzoylmethanes, such as 1-(4-tert-butylphenyl)-3-(4-methoxy-phenyl)propane-1,3-dione (for example Eusolex® 9020) or 4-isopropyldibenzoyl-methane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292) or isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethyl-hexyl 4-(dimethylamino)benzoate (for example Eusolex® 6007) or ethoxylated ethyl 4-aminobenzoate (for example Uvinul® P25), phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid; and further substances, such as 2-ethylhexyl 2-cyano-3,3-diphenylacrylate (for example Eusolex® OCR), 3,3'-(1,4-phenylenedimethylene)bis(7,7-dimethyl-2-oxo-bicyclo[2.2.1]hept-1-ylmethanesulfonic acid and salts thereof (for example Mexoryl® SX), 2,4,6-trianilino-(p-carbo-2'-ethylhexyl-1'-oxy)-1,3,5-triazine (for example Uvinul® T 150) and hexyl 2-(4-diethylamino-2-hydroxybenzoyl)benzoate (for example Uvinul® UVA Plus, BASF).

The compounds mentioned in the list should only be regarded as examples. It is of course also possible to use other UV filters.

These organic UV filters are generally incorporated into cosmetic formulations in an amount of from 0.5 to 10 percent by weight, preferably 1-8%.

Further suitable organic UV filters are, for example, 2-(2H-benzotriazol-2-yl)-4-methyl-6-(2-methyl-3-(1,3,3,3-tetramethyl-1-(tri-methylsilyloxy)disiloxanyl)propyl)phenol (for example Silatrizole®), 2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), α-(trimethylsilyl)-ω-[trimethylsilyl)oxy]poly[oxy(dimethyl [and about 6% of methyl[2-[p-[2,2-bis(ethoxycarbonyl)vinyl]phenoxy]-1-methyleneethyl] and approximately 1.5% of methyl[3-[p-[2,2-bis(ethoxycarbonyl)vinyl]phenoxy]-propenyl] and from 0.1 to 0.4% of (methylhydrogen)silylene]] (n≈60) (CAS No. 207 574-74-1)

2,2'-methylenebis(6-(2H-benzotriazol-2-yl)-4-(1,1,3,3-tetramethylbutyl)-phenol) (CAS No. 103 597-45-1)

2,2'-(1,4-phenylene)bis(1H-benzimidazole-4,6-disulfonic acid, mono-sodium salt) (CAS No. 180 898-37-7), 2,4-bis{[(4-(2-ethylhexyloxy)-2-hydroxyl]phenyl}-6-(4-methoxyphenyl)-1,3,5-triazine (CAS No. 103 597-45-, 187 393-00-6) and 2-ethylhexyl 4,4"-[(6-[4-((1,1-dimethylethyl)aminocarbonyl)phenylamino]-1,3,5-triazine-2,4-diyl)diimino] bis(benzoate) (for example Uvasorb® HEB).

Further suitable UV filters are also methoxyflavones corresponding to the earlier German patent application DE 10232595.2.

Organic UV filters are generally incorporated into cosmetic formulations in an amount of from 0.5 to 20 percent by weight, preferably 1-15%.

Conceivable inorganic UV filters are those from the group consisting of titanium dioxides, such as, for example, coated titanium dioxide (for example Eusolex® T-2000, Eusolex® T-AQUA), zinc oxides (for example Sachtotec®), iron oxides and also cerium oxides. These inorganic UV filters are generally incorporated into cosmetic compositions in an amount of from 0.5 to 20 percent by weight, preferably 2-10%.

Preferred compounds having UV-filtering properties are 3-(4'-methylbenzyl-idene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and its potassium, sodium and tri-ethanolamine salts.

Through combination of the compound of formula I with further UV filters, the protective action against harmful influences of UV radiation can be optimised.

Optimised compositions may comprise, for example, the combination of the organic UV filters 4'-methoxy-6-hydroxyflavone with 1-(4-tert-butylphenyl)-3-(4-methoxyphenyl)propane-1,3-dione and 3-(4'-methylbenzylidene)-dlcamphor. This combination gives rise to broad-band protection, which can be supplemented by the addition of inorganic UV filters, such as titanium dioxide micro-particles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in compositions according to the invention in amounts which ensure that the encapsulated UV filters are present in the composition in the above-indicated amounts.

The skin-protecting or skin-care active ingredients can in principle be any active ingredients known to the person skilled in the art.

In an embodiment of the present invention, particularly preferred active ingredients are pyrimidinecarboxylic acids and/or aryl oximes. Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoine ((S)-1,4,5,6-tetrahydro-2-methyl-4-pyrimidine-carboxylic acid) and hydroxyectoine ((S,S)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutically active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-ups, care creams and sunscreen compositions.

Preference is given here to the use of a pyrimidinecarboxylic acid of the following formula III

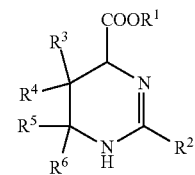

in which
$R^1$ is a radical H or $C_{1-8}$-alkyl,
$R^2$ is a radical H or $C_{1-4}$-alkyl,
and
$R^3$, $R^4$, $R^5$ and $R^6$ are each, independently of one another, a radical from the group consisting of H, OH, $NH_2$ and $C_{1-4}$-alkyl. Preference is given to the use of pyrimidinecarboxylic acids in which $R^2$ is a methyl or ethyl group, and $R^1$ or $R^5$ and $R^6$ are H.

Particular preference is given to the use of the pyrimidinecarboxylic acids ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidine-carboxylic acid). The compositions according to the invention preferably comprise pyrimidinecarboxylic acids of this type in amounts of up to 15% by weight. The pyrimidinecarboxylic acids are preferably employed here in ratios of from 100:1 to 1:100 with respect to the compound of formula I with ratios in the range from 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and integumentary appendages. Compositions according to the invention which, in addition to the compound of formula I additionally comprise an aryl oxime, preferably 2-hydroxy-5-methyllaurophenone oxime, exhibit surprising antiinflammatory suitability. The compositions here preferably comprise from 0.01 to 10% by weight of the aryl oxime, it being particularly preferred for the composition to comprise from 0.05 to 5% by weight of aryl oxime.

All compounds or components which can be used in the compositions are either known or commercially available or can be synthesised by known processes. The preparation of the compound of formula I is described in U.S. Pat. No. 6,596,758 B1 as Example 16.

The compound of formula I can be incorporated into cosmetic or dermatological compositions in the customary manner. Suitable compositions are those for external use, for example in the form of a cream, lotion or gel or as a solution which can be sprayed onto the skin. Suitable for internal use are administration forms such as capsules, coated tablets, powders, tablet solutions or solutions.

Use forms of the compositions according to the invention that may be mentioned are, for example, solutions, suspensions, emulsions, PIT emulsions, pastes, ointments, gels, creams, lotions, powders, soaps, surfactant-containing cleansing preparations, oils, aerosols and sprays. Examples of other use forms are sticks, shampoos and shower compositions. Any desired customary carriers, assistants and, if desired, further active ingredients may be added to the composition.

Preferred assistants originate from the group consisting of preservatives, anti-oxidants, stabilisers, solubilisers, vitamins, colorants and odour improvers.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary carriers, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkyl-amidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as fatty acid esters, fatty alcohols, silicone oils, natural oils, such as vegetable oils and oily plant extracts, paraffin oils or lanolin oils, or mixtures of these substances.

Further typical cosmetic use forms are also lipsticks, lip-care sticks, mascara, eyeliner, eye-shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
  mineral oils, mineral waxes;
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
  silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group consisting of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, or from the group consisting of esters of aromatic carboxylic acids and saturated and/or unsaturated, branched and/or unbranched alcohols having a chain length of from 3 to 30 carbon atoms. Ester oils of this type can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group consisting of branched and unbranched hydrocarbons and waxes, silicone oils, dialkyl ethers, or the group consisting of saturated and unsaturated, branched and unbranched alcohols, and fatty acid triglycerides, specifically the triglycerol esters of saturated and/or unsaturated, branched and/or unbranched alkane-carboxylic acids having a chain length of from 8 to 24, in particular 12 to 18, carbon atoms. The fatty acid triglycerides may advantageously be selected, for example, from the group consisting of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group consisting of 2-ethyl-hexyl isostearate, octyldodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol or glycerol, and, in particular, one or more thickeners, which may advantageously be selected from the group consisting of silicon dioxide, aluminium silicates, polysaccharides and derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group consisting of the alkylglucosides, acyl lactylates, betaines and coconut amphoacetates.

The alkylglucosides are themselves advantageously selected from the group consisting of the alkylglucosides which are distinguished by the structural formula

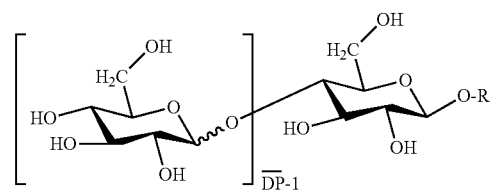

where
R is a branched or unbranched alkyl radical having from 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \Sigma \frac{p_i}{100} \cdot i$$

in which $p_1, p_2, p_3 \ldots p_i$ represent the proportion of mono-, di-, tri-. . . i-fold glucosylated products in percent by weight.

Products which are advantageous according to the invention are those having degrees of glucosylation of 1-2, particularly advantageously of from 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used for the purposes of the invention are selected from the group consisting of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and assistants or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group consisting of the substances which are distinguished by the structural formula

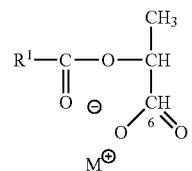

where
$R^1$ is a branched or unbranched alkyl radical having from 1 to 30 carbon atoms, and
$M^+$ is selected from the group consisting of the alkali metal ions and the group consisting of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group consisting of the substances which are distinguished by the structural formulae

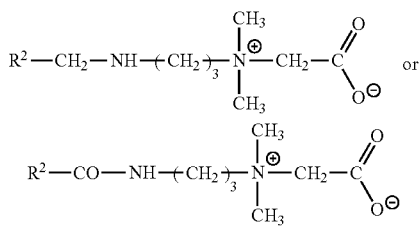

where
$R^2$ is a branched or unbranched alkyl radical having from 1 to 30 carbon atoms.

$R^2$ is particularly advantageously a branched or unbranched alkyl radical having from 6 to 12 carbon atoms.

For example, capramidopropylbetaine, for example the product Tego® Betain 810 from Th. Goldschmidt AG, is advantageous.

A coconut amphoacetate which is advantageous for the purposes of the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions are applied in sufficient amount to the skin and/or hair in the usual manner for cosmetics.

Cosmetic and dermatological compositions according to the invention may exist in various forms. Thus, they may be, for example, a solution, a water-free composition, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous according to the invention are, for example, O/W emulsifiers, principally from the group consisting of the substances having HLB values of 11 to 16, very particularly advantageously having HLB values of 14.5 to 15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageous for the purposes of the invention can be the following: fatty alcohols having from 8 to 30 carbon atoms, monoglycerol esters of saturated and/or unsaturated, branched and/or unbranched alkanecarboxylic acids having a chain length of from 8 to 24 carbon atoms, in particular 12 to 18 carbon atoms, diglycerol esters of saturated and/or unsaturated, branched and/or unbranched alkanecarboxylic acids having a chain length of from 8 to 24 carbon atoms, in particular 12 to 18 carbon atoms, monoglycerol ethers of saturated and/or unsaturated, branched and/or unbranched alcohols having a chain length of from 8 to 24 carbon atoms, in particular 12 to 18 carbon atoms, diglycerol ethers of saturated and/or unsaturated, branched and/or unbranched alcohols having a chain length of from 8 to 24 carbon atoms, in particular 12 to 18 carbon atoms, propylene glycol esters of saturated and/or unsaturated, branched and/or unbranched alkanecarboxylic acids having a chain length of from 8 to 24 carbon atoms, in particular 12 to 18 carbon atoms, and sorbitan esters of saturated and/or unsaturated, branched and/or unbranched alkanecarboxylic acids having a chain length of from 8 to 24 carbon atoms, in particular 12 to 18 carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate and glyceryl monocaprylate.

Preferred compositions according to the invention are particularly suitable for protecting human skin against ageing processes and against oxidative stress, i.e. against damage by free radicals, as are produced, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surfactants, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound of formula I comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent changes of colour shade, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling or treating the hair, in the form of a lotion or gel for brushing or blow-waving, in the form of a hair lacquer, permanent waving composition, colorant or bleach for the hair. Besides the compound of formula I the composition having light-protection properties may comprise various adjuvants used in this type of composition, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of a composition which is characterised in that the compound of formula I is mixed with a cosmetically or dermatologically or food-suitable carrier, and to the use of the compound of formula I for the preparation of a composition.

The compositions according to the invention can be prepared here with the aid of techniques which are well known to the person skilled in the art.

The mixing can result in dissolution, emulsification or dispersal of the compound of formula I.

The positive effects of the compound of formula I give rise to their particular suitability for use in cosmetic or pharmaceutical compositions.

The properties of the compound of formula I should likewise be regarded as positive for use in foods or as food supplements or as functional foods. The further explanations given for foods also apply correspondingly to food supplements and functional foods.

The foods which can be enriched with the compound of formula I include all materials which are suitable for consumption by animals or consumption by humans, for example vitamins and provitamins thereof, fats, minerals or amino acids. (The foods may be solid, but also liquid, i.e. in the form of a beverage).

The present invention accordingly furthermore relates to the use of the compound of formula I as food additive for human or animal nutrition, and to compositions which are foods or food supplements and comprise corresponding carriers.

Foods which can be enriched with the compound of formula I are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with the compound of formula I are corn or cereals from a single plant species and materials produced from plant species of this type, such as, for example, cereal syrup, rye flour, wheat flour or oat bran. Mixtures of foods of this type are also suitable for being enriched with the compound of formula I are, for example, multivitamin preparations, mineral mixtures or sweetened juice. As further examples of foods which can be enriched with the compound of formula I, mention may be made of food compositions, for example prepared cereals, biscuits, mixed drinks, foods prepared especially for children, such as yoghurt, diet foods, low-calorie foods or animal feeds.

The foods which can be enriched with the compound of formula I thus include all edible combinations of carbohydrates, lipids, proteins, inorganic elements, trace elements, vitamins, water or active metabolites of plants and animals.

The foods which can be enriched with the compound of formula I are preferably administered orally, for example in the form of meals, pills, tablets, capsules, powders, syrup, solutions or suspensions.

The foods according to the invention enriched with the compound of formula I can be prepared with the aid of techniques which are well known to the person skilled in the art.

Due to their action, the is preferable also suitable as medicament ingredients. the compound of formula I can be used, for example, for preventative treatment of inflammation and allergies of the skin and in certain cases for preventing certain types of cancer. The compound of formula I is particularly suitable for the preparation of a medicament for the treatment of inflammation, allergies and irritation, in particular of the skin. It is furthermore possible to prepare medicaments which act as a vein tonic, as cuperose inhibitor, as chemical, physical or actinic erythema inhibitor, as agent for the treatment of sensitive skin, as decongestant, as desiccant, as slimming agent, as antiwrinkle agent, as stimulator for the synthesis of components of the extracellular matrix, as strengthening agent for improving skin elasticity, and as anti-ageing agent. Furthermore, the compound of formula I exhibits antiallergic and antiinflammatory and antiirritative actions. They are therefore suitable for the preparation of medicaments for the treatment of inflammation or allergic reactions.

The invention is explained in greater detail below by means of examples. The invention can be carried out throughout the range claimed and is not restricted to the examples given here.

Moreover, the following examples are given in order to assist the skilled artisan to better understand the present invention by way of exemplification. The examples are not intended to limit the scope of protection conferred by the claims. The features, properties and advantages exemplified for the compounds, compositions and/or uses defined in the examples may be assigned to other compounds, compositions and/or uses not specifically described and/or defined in the examples, but falling under the scope of what is defined in the claims.

EXPERIMENTAL

In Vitro Biological Activities

Analysis of the activation of PPARα and PPARγ is based on the transfection of a DNA allowing the expression of a reporter gene (the gene of luciferase) under the control of the PPARs, either endogenous in the case of PPARγ or exogenous in the case of PPARα. The reporter plasmid J3TkLuc comprises three copies of the response element for PPARs of the human apo A-II gene (Staels, B et al. (1995), J. Clin. Invest., 95, 705-712) which are cloned upstream of the promoter of the thymidine kinase gene of the herpes simplex virus in the plasmid pGL3. This reporter gene was obtained by subcloning, in the plasmid pGL3, the plasmid J3TkCAT described above (Fajas, L et al. (1997), J. Biol. Chem., 272, 18779-18789). The cells used are green monkey CV1 cells transformed by the SV40 virus, which express PPARγ (Forman, B. et al. (1995), Cell, 83, 803-812), and human SK-Hep1 cells, which do not express PPARs. These cells were inoculated at the rate of 20,000 cells per well (96-well plates) and transfected with 150 ng of reporter DNA complexed with a mixture of lipids. In the case of the SK-Hep1 cells, an expression vector for PPARα, described by Sher, T. et al. (1993), Biochemistry, 32, 5598-5604, is cotransfected. After 5 hours, the cells are washed twice and incubated for 36 hours in the presence of the test compound in a fresh culture medium comprising 10% foetal calf serum. At the end of incubation, the cells are lysed and the luciferase activity is measured. This activity is expressed relative to the control value (data shown in Tables 1a and 1b TABLE 1a PPAR-alpha activity on human PPAR's TransActivation assay.
Fold Activation PPAR alpha

| 50 μm | 25 μm | 30 μm | 12.5 μm | 10 μm | 6.25 μm | 3 μm | 1 μm | 0.3 μm | 0.1 μm |
|---|---|---|---|---|---|---|---|---|---|
| 42.0 | 34.8 | 31.1 | 21.6 | 6.7 | 10.2 | 2.3 | 1.9 | 1.3 | 1.0 |

TABLE 1b

PPAR-gamma activity on human PPAR's TransActivation assay.
Fold Activation PPAR gamma

| 50 μm | 25 μm | 30 μm | 12.5 μm | 10 μm | 6.25 μm | 3 μm | 1 μm | 0.3 μm | 0.1 μm |
|---|---|---|---|---|---|---|---|---|---|
| 18.8 | 18.7 | 7.6 | 16.9 | 4.3 | 12.9 | 3.0 | 2.8 | 1.8 | 0.6 |

Hereinafter compound of formula I is also referred to as "Compound".

In Vitro Studies:
Inhibition of Melanin Synthesis in B16-V Melanoma Cells—Whitening Activity B16-V melanoma cells were incubated for 72 h with assay medium containing different amounts of test substances. The concentration depends on the results of the MTT-Assay. Only concentrations without effect on viability (after 24 h incubation) were used for further melanin evaluation. Every 24 hours medium was changed and replaced by fresh assay medium containing the compounds and alpha-MSH (stimulation of melanin synthesis). The cell number was determined and the cells got lysed using 1M NaOH. Afterwards the amount of melanin was measured at 405 nm with a microplatereader (Safire2™, Tecan). Different concentrations of synthetic melanin were used to produce a calibration curve. Melanin content was expressed as pg/cell.

The test results are shown in FIG. 1:
As apparent from FIG. 1 Compound as PPAR-alpha and -gamma agonist show a superb melanin inhibiting activity. Furthermore the substance is significantly better than kojic acid.

Formulation Examples

Formulations for compositions, preferably preferably non-therapeutic compositions, cosmetic compositions and/or topical compositions, comprising the compound of formula I are shown by way of example below. For some commercially available compounds the INCI names are given. UV-Pearls™ OMC stands for the composition with the INCI: water (for EU: Aqua), Ethylhexyl Methoxycinnamate, Silica, PVP, Chlorphenesin, BHT; this composition is commercially available under the name Eusolex®UV Pearl™ OMC from Merck KGaA, Darmstadt.

The other UV Pearl products indicated in the tables are each of analogous composition with OMC replaced by the UV filter indicated.

TABLE 2a

| W/O-Emulsion (weight-%) | | | | | | |
|---|---|---|---|---|---|---|
| | 1-1 | 1-2 | 1-3 | 1-4 | 1-5 | 1-9 |
| Titanium dioxide | | 2 | 5 | | | |
| Compound | 0.1 | 0.2 | 0.3 | 0.4 | 0.7 | 0.5 |
| Bisabolol | | | 0.1 | | | |
| Ectoine | 0.1 | | | | | |
| Tiliroside | | | | 0.1 | | |
| Allantoin | | | | | 0.1 | |
| Urea | | | | | | 2 |
| Zinc oxide | | | | | | 2 |
| UV-Pearl, OMC | 30 | 15 | 15 | 15 | 15 | 15 |
| Polyglyceryl-3-Dimerate | 3 | 3 | 3 | 3 | 3 | 3 |
| Cera Alba | 0.3 | 0.3 | 0.3 | 0.3 | 0.3 | 0.3 |
| Hydrogenated Castor Oil | 0.2 | 0.2 | 0.2 | 0.2 | 0.2 | 0.2 |
| Paraffinium Liquidum | 7 | 7 | 7 | 7 | 7 | 7 |
| Caprylic/Capric Triglyceride | 7 | 7 | 7 | 7 | 7 | 7 |
| Hexyl Laurate | 4 | 4 | 4 | 4 | 4 | 4 |
| PVP/Eicosene Copolymer | 2 | 2 | 2 | 2 | 2 | 2 |
| Propylene Glycol | 4 | 4 | 4 | 4 | 4 | 4 |
| Magnesium Sulfate | 0.6 | 0.6 | 0.6 | 0.6 | 0.6 | 0.6 |
| Tocopherol | 0.5 | 0.5 | 0.5 | 0.5 | 0.5 | 0.5 |
| Tocopheryl Acetate | 0.5 | 0.5 | 0.5 | 0.5 | 0.5 | 0.5 |
| Cyclomethicone | 0.5 | 0.5 | 0.5 | 0.5 | 0.5 | 0.5 |
| Propylparabene | 0.05 | 0.05 | 0.05 | 0.05 | 0.05 | 0.05 |
| Methylparabene | 0.15 | 0.15 | 0.15 | 0.15 | 0.15 | 0.15 |
| Water | ad 100 | ad 100 | ad 100 | ad 100 | ad 100 | ad 100 |

TABLE 2b

| | 1-11 | 1-12 | 1-13 | 1-14 | 1-15 | 1-16 | 1-17 | 1-18 |
|---|---|---|---|---|---|---|---|---|
| Titanium dioxide | 3 | | 2 | | 3 | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| Compound | 0.1 | 0.2 | 0.3 | 0.5 | 0.7 | 0.2 | 0.4 | 0.2 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |

TABLE 2b-continued

|  | 1-11 | 1-12 | 1-13 | 1-14 | 1-15 | 1-16 | 1-17 | 1-18 |
|---|---|---|---|---|---|---|---|---|
| Dicocoyl Pentyerythrityl Citrate (and) Sorbitan Sesquioleate (and) Cera Alba (and) Aluminium Stearate |  |  |  |  | 6 | 6 | 6 | 6 |
| PEG-7 Hydrogenated Castor Oil |  |  |  |  | 1 | 1 | 1 | 1 |
| Zinc Stearate |  |  |  |  | 2 | 2 | 2 | 2 |
| Oleyl Erucate |  |  |  |  | 6 | 6 | 6 | 6 |
| Decyl Oleate |  |  |  |  | 6 | 6 | 6 | 6 |
| Dimethicone |  |  |  |  | 5 | 5 | 5 | 5 |
| Tromethamine |  |  |  |  | 1 | 1 | 1 | 1 |
| Glycerin |  |  |  |  | 5 | 5 | 5 | 5 |
| Allantoin |  |  |  |  | 0.2 | 0.2 | 0.2 | 0.2 |
| Water | ad 100 | ad 100 | ad 100 | ad 100 | ad 100 | ad 100 | ad 100 | ad 100 |

TABLE 3a

O/W-Emulsion, (weight-%)

|  | 2-1 | 2-2 | 2-3 | 2-4 | 2-5 | 2-6 | 2-7 |
|---|---|---|---|---|---|---|---|
| Titanium dioxide |  | 2 | 5 |  |  |  |  |
| Methylene Bis-Benztriazolyl Tetramethylbutylphenol |  |  |  |  |  | 1 | 2 |
| Compound | 0.1 | 0.2 | 0.3 | 0.4 | 0.5 | 1 | 2 |
| 4-Methylbenzyliden Camphor | 2 |  | 3 |  | 4 |  | 3 |
| BMDBM | 1 | 3 |  | 3 | 3 |  | 3 |
| Stearyl Alcohol (and) Steareth-7 (and) Steareth-10 | 3 | 3 | 3 | 3 | 3 | 3 | 3 |
| Glyceryl Stearate (and) Ceteth-20 | 3 | 3 | 3 | 3 | 3 | 3 | 3 |
| Glyceryl Stearate | 3 | 3 | 3 | 3 | 3 | 3 | 3 |
| Microwax | 1 | 1 | 1 | 1 | 1 | 1 | 1 |
| Cetearyl Octanoate | 11.5 | 11.5 | 11.5 | 11.5 | 11.5 | 11.5 | 11.5 |
| Caprylic/Capric Triglyceride | 6 | 6 | 6 | 6 | 6 | 6 | 6 |
| Oleyl Oleate | 6 | 6 | 6 | 6 | 6 | 6 | 6 |
| Propylene Glycol | 4 | 4 | 4 | 4 | 4 | 4 | 4 |
| Propylparabene | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 |
| Tromethamine |  |  |  |  | 1.8 |  |  |
| Water | ad 100 | ad 100 | ad 100 | ad 100 | ad 100 | ad 100 | ad 100 |

TABLE 3b

|  | 2-11 | 2-12 | 2-13 | 2-14 | 2-15 | 2-16 | 2-17 | 2-18 |
|---|---|---|---|---|---|---|---|---|
| Titanium dioxide | 3 |  | 2 |  |  |  | 2 | 5 |
| Benzylidene malonate polysiloxane |  | 1 | 0.5 |  |  |  |  |  |
| Methylene Bis-Benztriazolyl Tetramethylbutylphenol | 1 | 1 | 0.5 |  |  |  |  |  |
| Compound | 5 | 5 | 5 | 5 | 5 | 5 | 5 | 5 |
| Zinc oxide |  |  | 2 |  |  |  |  |  |
| UV-Pearl, OMC | 15 | 15 | 15 | 30 | 30 | 30 | 15 | 15 |
| 4-Methylbenzyliden Camphor |  |  |  |  | 3 |  |  |  |
| BMDBM |  |  |  |  |  | 1 |  |  |
| Phenylbenzimidazole Sulfonic Acid |  |  |  |  |  |  | 4 |  |
| Stearyl Alcohol (and) Steareth-7 (and) Steareth-10 | 3 | 3 | 3 | 3 |  |  |  |  |
| Glyceryl Stearate (and) Ceteth-20 | 3 | 3 | 3 | 3 |  |  |  |  |
| Glyceryl Stearate | 3 | 3 | 3 | 3 |  |  |  |  |
| Microwax | 1 | 1 | 1 | 1 |  |  |  |  |
| Cetearyl Octanoate | 11.5 | 11.5 | 11.5 | 11.5 |  |  |  |  |
| Caprylic/Capric Triglyceride | 6 | 6 | 6 | 6 | 14 | 14 | 14 | 14 |
| Oleyl Oleate | 6 | 6 | 6 | 6 |  |  |  |  |
| Propylene Glycol | 4 | 4 | 4 | 4 |  |  |  |  |
| Glyceryl Stearate SE |  |  |  |  | 6 | 6 | 6 | 6 |
| Stearic Acid |  |  |  |  | 2 | 2 | 2 | 2 |
| *Persea Gratissima* |  |  |  |  | 8 | 8 | 8 | 8 |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Tromethamine |  |  |  |  | 1.8 |  |  |  |
| Glycerin |  |  |  |  | 3 | 3 | 3 | 3 |
| Water | ad 100 | ad 100 | ad 100 | ad 100 | ad 100 | ad 100 | ad 100 | ad 100 |

TABLE 4

Gel, (weight-%)

| | 3-1 | 3-2 | 3-3 | 3-4 | 3-5 | 3-6 | 3-7 | 3-8 | 3-9 | 3-10 |
|---|---|---|---|---|---|---|---|---|---|---|
| Titanium dioxide | | 2 | 5 | | | | | | | 3 |
| Compound | 0.05 | 0.1 | 0.3 | 0.2 | 0.5 | 0.6 | 0.7 | 0.8 | 0.9 | 1 |
| Benzylidene malonate polysiloxane | | | 1 | 1 | 2 | | | | 1 | 1 |
| Methylene Bis-Benztriazolyl Tetramethylbutyl-phenol | | 1 | | | | 1 | 2 | 1 | | |
| Zinc oxide | | | | 2 | | | | 5 | 2 | |
| UV-Pearl, Ethylhexyl Mehtoxycinnamat | 30 | 15 | 15 | 15 | 15 | 15 | 15 | 15 | 15 | 15 |
| 4-Methylbenzyliden Camphor | | | | | 2 | | | | | |
| Butylmethoxydibenzoyl-methane | | 1 | | | | | | | | |
| Phenylbenzimidazole Sulfonic Acid | | | 4 | | | | | | | |
| *Prunus Dulcis* | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | ad 100 | ad 100 | ad 100 | ad 100 | ad 100 | ad 100 | ad 100 | ad 100 | ad 100 | ad 100 |

TABLE 5a

O/W emulsions (weight-%)

| | INCI/Chem.-Name | 4-1 | 4-2 | 4-3 | 4-4 | 4-5 | 4-6 |
|---|---|---|---|---|---|---|---|
| A | ARACHIDYL ALCOHOL, BEHENYL ALCOHOL, ARACHIDYL-GLUCOSIDE | 3.00 | 3.00 | 3.00 | 3.00 | 3.00 | 3.00 |
| | PHENYLETHYL BENZOATE | 10.00 | 10.00 | 10.00 | 10.00 | 10.00 | 10.00 |
| | ISOPROPYL-PHTALIMIDE, BUTYLPHTALIDE | 2.00 | 2.00 | 2.00 | 2.00 | 2.00 | 2.00 |
| | ISOEICOSANE | 1.00 | 1.00 | 1.00 | 1.00 | 1.00 | 1.00 |
| | HYDROGENATED POLYDECENE | 1.00 | 1.00 | 1.00 | 1.00 | 1.00 | 1.00 |
| | Compound | 0.2 | 0.1 | 0.3 | 0.5 | 1 | 5 |
| B | GLYCERIN, AQUA | 3.00 | 3.00 | 3.00 | 3.00 | 3.00 | 3.00 |
| | AQUA (WATER) | Ad 100 | Ad 100 | Ad 100 | Ad 100 | Ad 100 | Ad 100 |
| C | HYDROXYETHYL ACRYLATE/SODIUM ACRYLOYL-DIMETHYLTAURATE COPOLYMER, SQUALANE, POLYSORBATE 60 | 2.00 | 2.00 | 2.00 | 2.00 | 2.00 | 2.00 |
| D | PROPYLENE GLYCOL, DIAZOLIDINYL UREA, METHYLPARABEN, PROPYLPARABEN | 0.75 | 0.75 | 0.75 | 0.75 | 0.75 | 0.75 |

TABLE 5b

| INCI | 4-7 | 4-8 | 4-9 | 4-10 | 4-11 | 4-12 | 4-13 | 4-14 | 4-15 | 4-16 |
|---|---|---|---|---|---|---|---|---|---|---|
| POLYGLYCERYL-3 METHYLGLUCOSE DISTEARATE | 3.00 | 3.00 | 3.00 | 3.00 | 3.00 | 3.00 | 3.00 | 3.00 | 3.00 | 3.00 |
| STEARYL ALCOHOL | 3.00 | 3.00 | 3.00 | 3.00 | 3.00 | 3.00 | 3.00 | 3.00 | 3.00 | 3.00 |
| GLYCERYL STEARATE | 2.00 | 2.00 | 2.00 | 2.00 | 2.00 | 2.00 | 2.00 | 2.00 | 2.00 | 2.00 |
| DECYL COCOATE | 5.00 | 5.00 | 5.00 | 5.00 | 5.00 | 5.00 | 5.00 | 5.00 | 5.00 | 5.00 |
| CETEARYL ETHYLHEXANOATE | 5.00 | 5.00 | 5.00 | 5.00 | 5.00 | 5.00 | 5.00 | 5.00 | 5.00 | 5.00 |
| C12-15 ALKYL BENZOATE | 8.50 | 8.50 | 8.50 | 8.50 | 8.50 | 8.50 | 8.50 | 8.50 | 8.50 | 8.50 |

TABLE 5b-continued

| INCI | 4-7 | 4-8 | 4-9 | 4-10 | 4-11 | 4-12 | 4-13 | 4-14 | 4-15 | 4-16 |
|---|---|---|---|---|---|---|---|---|---|---|
| XANTHAN GUM | 0.20 | 0.20 | 0.20 | 0.20 | 0.20 | 0.20 | 0.20 | 0.20 | 0.20 | 0.20 |
| PROPYLPARABEN | 0.05 | 0.05 | 0.05 | 0.05 | 0.05 | 0.05 | 0.05 | 0.05 | 0.05 | 0.05 |
| Compound | 0.25 | 0.5 | 0.3 | 0.1 | 0.2 | 1 | 2 | 5 | 0.35 | 0.05 |
| GLYCERIN | 6.00 | 6.00 | 6.00 | 6.00 | 6.00 | 6.00 | 6.00 | 6.00 | 6.00 | 6.00 |
| METHYLPARABEN | 0.15 | 0.15 | 0.15 | 0.15 | 0.15 | 0.15 | 0.15 | 0.15 | 0.15 | 0.15 |
| AQUA (WATER) | Ad 100 | Ad 100 | Ad 100 | Ad 100 | Ad 100 | Ad 100 | Ad 100 | Ad 100 | Ad 100 | Ad 100 |

TABLE 6

W/O emulsions, (weight-%)

|  | 5-1 | 5-2 | 5-3 | 5-4 | 5-6 | 5-7 | 5-8 | 5-9 | 5-10 |
|---|---|---|---|---|---|---|---|---|---|
| POLYGLYCERYL-4 ISOSTEARATE | 1.00 | 1.00 | 1.00 | 1.00 | 1.00 | 1.00 | 1.00 | 1.00 | 1.00 |
| CETYL PEG/PPG-10/1 DIMETHICONE | 2.00 | 2.00 | 2.00 | 2.00 | 2.00 | 2.00 | 2.00 | 2.00 | 2.00 |
| CERESIN (MICROCRYSTALLINE WAX) | 1.50 | 1.50 | 1.50 | 1.50 | 1.50 | 1.50 | 1.50 | 1.50 | 1.50 |
| HYDROGENATED CASTOR OIL | 0.50 | 0.50 | 0.50 | 0.50 | 0.50 | 0.50 | 0.50 | 0.50 | 0.50 |
| DECYL OLEATE | 10.00 | 10.00 | 10.00 | 10.00 | 10.00 | 10.00 | 10.00 | 10.00 | 10.00 |
| CAPRYLIC/CAPRIC TRIGLYCERIDE | 10.00 | 10.00 | 10.00 | 10.00 | 10.00 | 10.00 | 10.00 | 10.00 | 10.00 |
| OCTYLDODECYL MYRISTATE | 5.00 | 5.00 | 5.00 | 5.00 | 5.00 | 5.00 | 5.00 | 5.00 | 5.00 |
| Compound | 0.1 | 0.25 | 0.4 | 0.2 | 0.3 | 0.5 | 0.6 | 0.7 | 1 |
| GLYCERIN | 2.00 | 2.00 | 2.00 | 2.00 | 2.00 | 2.00 | 2.00 | 2.00 | 2.00 |
| MAGNESIUM SULFATE | 1.00 | 1.00 | 1.00 | 1.00 | 1.00 | 1.00 | 1.00 | 1.00 | 1.00 |
| AQUA (WATER) | 66.25 | 66.25 | 66.25 | 66.25 | 66.25 | 66.25 | 66.25 | 66.25 | 66.25 |
| PROPYLENE GLYCOL, DIAZOLIDINYL UREA, METHYLPARABEN, PROPYLPARABEN | 0.50 | 0.50 | 0.50 | 0.50 | 0.50 | 0.50 | 0.50 | 0.50 | 0.50 |

TABLE 7 ointment (water-free)

|  | 6-1 | 6-2 | 6-3 | 6-4 | 6-5 | 6-6 | 6-7 | 6-8 | 6-9 | 6-10 |
|---|---|---|---|---|---|---|---|---|---|---|
| MICROWAX | 16.00 | 16.00 | 16.00 | 16.00 | 16.00 | 16.00 | 16.00 | 16.00 | 16.00 | 16.00 |
| *BUTYROSPERMUM PARKII* (SHEA BUTTER) | 13.00 | 13.00 | 13.00 | 13.00 | 13.00 | 13.00 | 13.00 | 13.00 | 13.00 | 13.00 |
| C12-15 ALKYL BENZOATE | 28.00 | 28.00 | 28.00 | 28.00 | 28.00 | 28.00 | 28.00 | 28.00 | 28.00 | 28.00 |
| CAPRYLIC/CAPRIC TRIGLYCERIDE | 27.25 | 27.25 | 27.25 | 27.25 | 27.25 | 27.25 | 27.25 | 27.25 | 27.25 | 27.25 |
| DIBUTYL ADIPATE | 15.00 | 15.00 | 15.00 | 15.00 | 15.00 | 15.00 | 15.00 | 15.00 | 15.00 | 15.00 |
| Compound | 0.1 | 0.25 | 0.4 | 0.3 | 1 | 0.5 | 0.9 | 0.6 | 0.75 | 5 |

TABLE 8

Oil-Gel (water-free)

| INCI | 7-1 | 7-2 | 7-3 | 7-4 | 7-5 | 7-6 | 7-7 | 7-8 | 7-9 | 7-10 |
|---|---|---|---|---|---|---|---|---|---|---|
| OCTOCRYLENE | 10.00 | 10.00 | 10.00 | 10.00 | 10.00 | 10.00 | 10.00 | 10.00 | 10.00 | 10.00 |
| BUTYL METHOXYDI-BENZOYL-METHANE | 3.00 | 3.00 | 3.00 | 3.00 | 3.00 | 3.00 | 3.00 | 3.00 | 3.00 | 3.00 |
| TOCOPHERYL ACETATE | 1.00 | 1.00 | 1.00 | 1.00 | 1.00 | 1.00 | 1.00 | 1.00 | 1.00 | 1.00 |
| TOCOPHEROL | 0.50 | 0.50 | 0.50 | 0.50 | 0.50 | 0.50 | 0.50 | 0.50 | 0.50 | 0.50 |

TABLE 8-continued

| | Oil-Gel (water-free) | | | | | | | | | |
|---|---|---|---|---|---|---|---|---|---|---|
| INCI | 7-1 | 7-2 | 7-3 | 7-4 | 7-5 | 7-6 | 7-7 | 7-8 | 7-9 | 7-10 |
| ASCORBYL PALMITATE | 0.20 | 0.20 | 0.20 | 0.20 | 0.20 | 0.20 | 0.20 | 0.20 | 0.20 | 0.20 |
| GLYCERYL STEARATE | 0.10 | 0.10 | 0.10 | 0.10 | 0.10 | 0.10 | 0.10 | 0.10 | 0.10 | 0.10 |
| DIETHYLHEXYL CARBONATE | 2.00 | 2.00 | 2.00 | 2.00 | 2.00 | 2.00 | 2.00 | 2.00 | 2.00 | 2.00 |
| DECYL OLEATE | 2.00 | 2.00 | 2.00 | 2.00 | 2.00 | 2.00 | 2.00 | 2.00 | 2.00 | 2.00 |
| TRIDECYL SALICYLATE | 4.00 | 4.00 | 4.00 | 4.00 | 4.00 | 4.00 | 4.00 | 4.00 | 4.00 | 4.00 |
| Compound | 0.1 | 0.25 | 0.4 | 0.3 | 0.5 | 1 | 0.7 | 0.6 | 0.8 | 1 |
| ECTOIN | 0.30 | 0.30 | 0.30 | 0.30 | 0.30 | 0.30 | 0.30 | 0.30 | 0.30 | 0.30 |
| CITRIC ACID | 0.10 | 0.10 | 0.10 | 0.10 | 0.10 | 0.10 | 0.10 | 0.10 | 0.10 | 0.10 |
| AQUA (WATER), CI 17200 | 0.30 | 0.30 | 0.30 | 0.30 | 0.30 | 0.30 | 0.30 | 0.30 | 0.30 | 0.30 |
| GLYCERIN | 1.00 | 1.00 | 1.00 | 1.00 | 1.00 | 1.00 | 1.00 | 1.00 | 1.00 | 1.00 |
| HYDROXY-PROPYLCELLULOSE | 2.00 | 2.00 | 2.00 | 2.00 | 2.00 | 2.00 | 2.00 | 2.00 | 2.00 | 2.00 |
| PROPYLENE GLYCOL | 3.00 | 3.00 | 3.00 | 3.00 | 3.00 | 3.00 | 3.00 | 3.00 | 3.00 | 3.00 |
| CYCLOHEXA-SILOXANE | 9.00 | 9.00 | 9.00 | 9.00 | 9.00 | 9.00 | 9.00 | 9.00 | 9.00 | 9.00 |
| ALCOHOL | Ad 100 | Ad 100 | Ad 100 | Ad 100 | Ad 100 | Ad 100 | Ad 100 | Ad 100 | Ad 100 | Ad 100 |

The invention claimed is:

1. A method for
the cosmetic application of a composition, comprising cosmetically applying said composition to a subject,
or
hair care and/or hair follicle development, comprising applying a composition in an effective amount to a subject in need thereof,
or
the care, preservation or improvement of the general state of the skin or hair, comprising applying a composition in an effective amount to a subject in need thereof,
or
skin lightening and/or skin whitening, comprising applying a composition in an effective amount to a subject in need thereof,
or
the reduction of skin unevenness, wrinkles, fine lines, rough skin or large-pored skin, comprising applying a composition in an effective amount to a subject in need thereof,
or
reducing harmful effects of UV rays on the skin, comprising applying a composition in an effective amount to a subject in need thereof,
or
treating a skin disease selected from the group consisting of acne vulgaris, acne comedonica, polymorphic acne, acne rosaceae, nodular acne, acne conglobata, age-related acne, acne occurring as a side effect, acne solaris, medicament-related acne, acne professionalis, ichthyosis, ichthyosiform states, Darier's disease, keratosis palmoplantaris, leukoplakia, leukoplakiform states, skin and mucosal (buccal) eczema (lichen), psoriasis relating to the skin, mucous membranes and finger- and toenails, psoriatic rheumatism, skin atopy, eczema, respiratory atopy, and hypertrophy of the gums, comprising applying a composition in an effective amount to a subject in need thereof, wherein the composition comprises a compound of formula of I

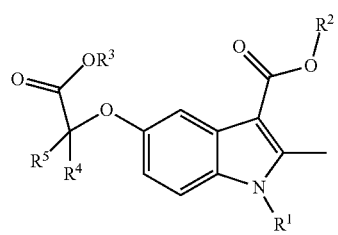

wherein
$R^1$, $R^2$ and $R^3$ are identical or different and each is H or alkyl of 1-6 carbon atoms,
$R^4$ is H or methyl,
$R^5$ is phenyl or chlorophenyl,
and/or physiologically acceptable salts thereof
and one or more topically acceptable vehicles.

2. A method according to claim 1, wherein the composition comprises 2-Phenyl-2-(1-isobutyl-2-methyl-3-ethoxycarbonyl-5-indolyloxy)-propionic acid and/or a physiologically acceptable salt thereof.

3. A method according to claim 1, wherein the composition comprises
a) a compound of formula of I and/or a physiologically acceptable salt thereof,
b) one or more skin-tolerated vehicles, and
c) optionally one or more further active compounds having a skin-care and/or inflammation-inhibiting action.

4. A method according to claim 1, wherein the composition comprises 0.00001 per cent by weight to 10 per cent by weight of a compound of formula of I and/or a physiologically acceptable salt thereof.

5. A method according to claim 1, wherein the composition comprises at least one further skin-care ingredient and at least one carrier which is suitable for topical applications.

6. A method according to claim 1, wherein the composition comprises as a further skin-care ingredient ectoine.

7. A method according to claim 1, which is for the cosmetic application of a composition.

8. A method according to claim 1, which is for hair care and/or hair follicle development.

9. A method according to claim 1, which is for the care, preservation or improvement of the general state of the skin or hair.

10. A method according to claim 1, which is for skin lightening and/or skin whitening.

11. A method according to claim 1, which is for the reduction of skin unevenness, wrinkles, fine lines, rough skin or large-pored skin.

12. A method according to claim 1, which is for reducing harmful effects of UV rays on the skin.

13. A method according to claim 1, which is for treating a skin disease selected from the group consisting of acne vulgaris, acne comedonica, polymorphic acne, acne rosaceae, nodular acne, acne conglobata, age-related acne, acne occurring as a side effect, acne solaris, medicament-related acne, acne professionalis, ichthyosis, ichthyosiform states, Darier's disease, keratosis palmoplantaris, leukoplakia, leukoplakiform states, skin and mucosal (buccal) eczema (lichen), psoriasis relating to the skin, mucous membranes and finger- and toenails, psoriatic rheumatism, skin atopy, eczema, respiratory atopy, and hypertrophy of the gums.

14. A method according to claim 1, wherein the composition comprises as a further skin-care ingredient ectoine in an amount of 0.01 to 10 per cent by weight.

15. A method according to claim 1, wherein the composition comprises as a further skin-care ingredient ectoine in an amount of 0.1 to 5 per cent by weight.

16. A method according to claim 1, wherein the composition comprises as a further skin-care ingredient ectoine in an amount of 0.1 to 2 per cent by weight.

* * * * *